United States Patent
Quearry et al.

(10) Patent No.: US 9,980,699 B2
(45) Date of Patent: May 29, 2018

(54) SHAPED ECHOGENIC NEEDLE GROOVE

(71) Applicant: Cook Medical Technologies LLC, Bloomington, IN (US)

(72) Inventors: Benjaman B. Quearry, Bloomington, IN (US); Fionan Keady, Castletroy (IE)

(73) Assignee: Cook Medical Technologies LLC, Bloomington, IN (US)

( * ) Notice: Subject to any disclaimer, the term of this patent is extended or adjusted under 35 U.S.C. 154(b) by 172 days.

(21) Appl. No.: 14/813,167

(22) Filed: Jul. 30, 2015

(65) Prior Publication Data
US 2016/0074130 A1    Mar. 17, 2016

Related U.S. Application Data

(60) Provisional application No. 62/049,573, filed on Sep. 12, 2014.

(51) Int. Cl.
*A61B 8/14* (2006.01)
*A61B 8/08* (2006.01)
(Continued)

(52) U.S. Cl.
CPC ........ *A61B 8/0841* (2013.01); *A61B 10/0233* (2013.01); *A61B 19/54* (2013.01);
(Continued)

(58) Field of Classification Search
CPC combination set(s) only.
See application file for complete search history.

(56) References Cited

U.S. PATENT DOCUMENTS

| 4,055,167 A | 12/1977 | Bernstein |
| 4,401,124 A | 8/1983 | Guess et al. |

(Continued)

FOREIGN PATENT DOCUMENTS

| DE | 20 2009 005135 U1 | 2/2010 |
| WO | WO 2008/062451 A2 | 5/2008 |

(Continued)

OTHER PUBLICATIONS

European Patent Application 15183750.7 Extended Search Report dated May 31, 2016. 10 pages.
(Continued)

*Primary Examiner* — Joel F Brutus
(74) *Attorney, Agent, or Firm* — Woodard, Emhardt, Moriarty, McNett & Henry, LLP

(57) ABSTRACT

Disclosed are embodiments of devices and methods for providing enhanced echogenicity to medical devices. At least two adjacent echogenic features with an intervening section positioned between the echogenic features are formed as a helical groove in a medical device surface. Each of the echogenic features has a depression that spans between first and second transition lips. In one form, each depression includes a steep portion adjacent a shallow portion wherein the steep portion has a first radius and the shallow portion has a second radius that is larger than the first radius such that the radii capture different wavelengths of ultrasound. The intervening section has a planar surface in which the first and second transition lips do not extend above. In one form, each of the at least two echogenic features has a length that is within 0.1 mm of a length of the intervening section.

20 Claims, 2 Drawing Sheets

(51) Int. Cl.
*A61B 10/02* (2006.01)
*A61B 19/00* (2006.01)
A61B 17/34 (2006.01)
A61B 90/00 (2016.01)

(52) U.S. Cl.
CPC .............. *A61B 2017/3413* (2013.01); *A61B 2019/5425* (2013.01); *A61B 2090/3925* (2016.02)

(56) References Cited

U.S. PATENT DOCUMENTS

| | | |
|---|---|---|
| 4,627,444 A | 12/1986 | Brooker |
| 4,702,260 A | 10/1987 | Wang |
| 4,791,937 A | 12/1988 | Wang |
| 4,900,300 A | 2/1990 | Lee |
| 4,903,709 A | 2/1990 | Skinner |
| 4,989,614 A | 2/1991 | Dejter, Jr. et al. |
| 4,991,592 A | 2/1991 | Christ |
| 5,106,364 A | 4/1992 | Hayafuji et al. |
| 5,201,314 A * | 4/1993 | Bosley, Jr. ............. A01K 85/00 600/431 |
| 5,320,110 A | 6/1994 | Wang |
| 5,449,001 A | 9/1995 | Terwilliger |
| 5,458,112 A | 10/1995 | Weaver |
| 5,470,308 A | 11/1995 | Edwards et al. |
| 5,807,304 A | 9/1998 | Cockburn |
| 5,817,033 A | 10/1998 | DeSantis et al. |
| 5,865,765 A | 2/1999 | Mohajer |
| 5,967,988 A | 10/1999 | Briscoe et al. |
| 5,971,939 A | 10/1999 | DeSantis et al. |
| 6,018,676 A | 1/2000 | Davis et al. |
| 6,053,870 A | 4/2000 | Fulton, III |
| 6,689,043 B1 | 2/2004 | McIntire et al. |
| 6,709,408 B2 | 3/2004 | Fisher |
| 6,749,554 B1 | 6/2004 | Snow et al. |
| 7,083,566 B2 | 8/2006 | Tornes et al. |
| 2003/0158480 A1* | 8/2003 | Tornes .................. A61B 90/39 600/437 |
| 2006/0047254 A1* | 3/2006 | Akahoshi ............ A61F 9/00745 604/272 |
| 2009/0054773 A1 | 2/2009 | Shizuka |
| 2009/0118641 A1 | 5/2009 | Van Dam et al. |
| 2009/0177114 A1 | 7/2009 | Chin et al. |
| 2010/0168684 A1* | 7/2010 | Ryan ................ A61B 10/0233 604/272 |
| 2012/0059247 A1 | 3/2012 | Speeg et al. |
| 2012/0253228 A1 | 10/2012 | Schembre et al. |
| 2012/0253297 A1* | 10/2012 | Matsuzawa ........... A61M 5/158 604/272 |
| 2013/0267942 A1 | 10/2013 | Fulton, III |
| 2014/0221828 A1 | 8/2014 | McKinnis et al. |
| 2014/0336687 A1 | 11/2014 | Iwase et al. |

FOREIGN PATENT DOCUMENTS

| | | |
|---|---|---|
| WO | WO 2010/012023 A1 | 2/2010 |
| WO | WO 2013/084814 A1 | 6/2013 |

OTHER PUBLICATIONS

European Patent Application 15183750.7 Partial Search Report dated Jan. 25, 2016.

* cited by examiner

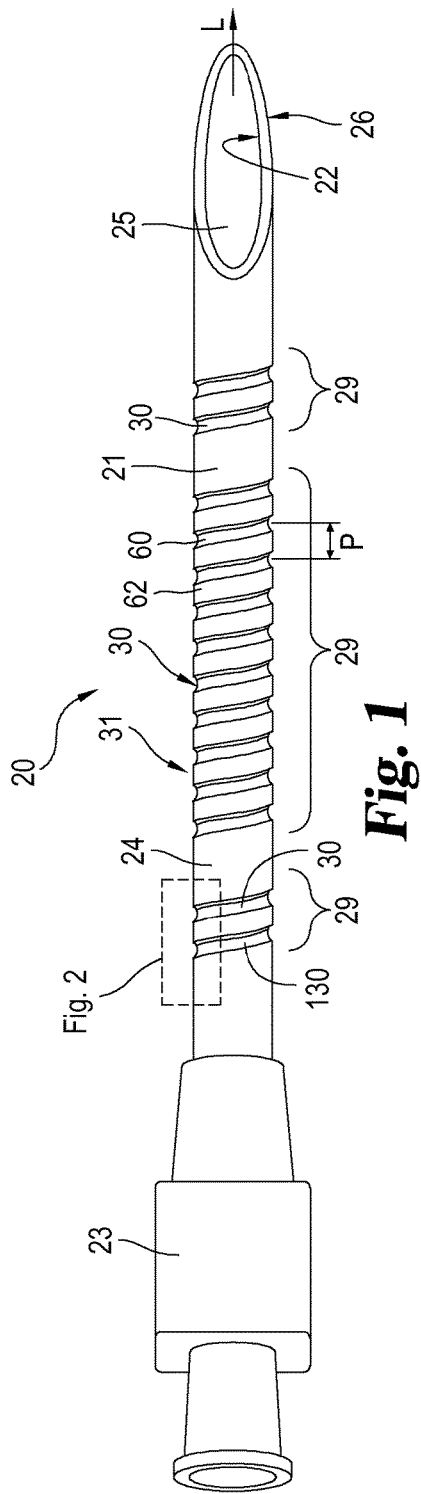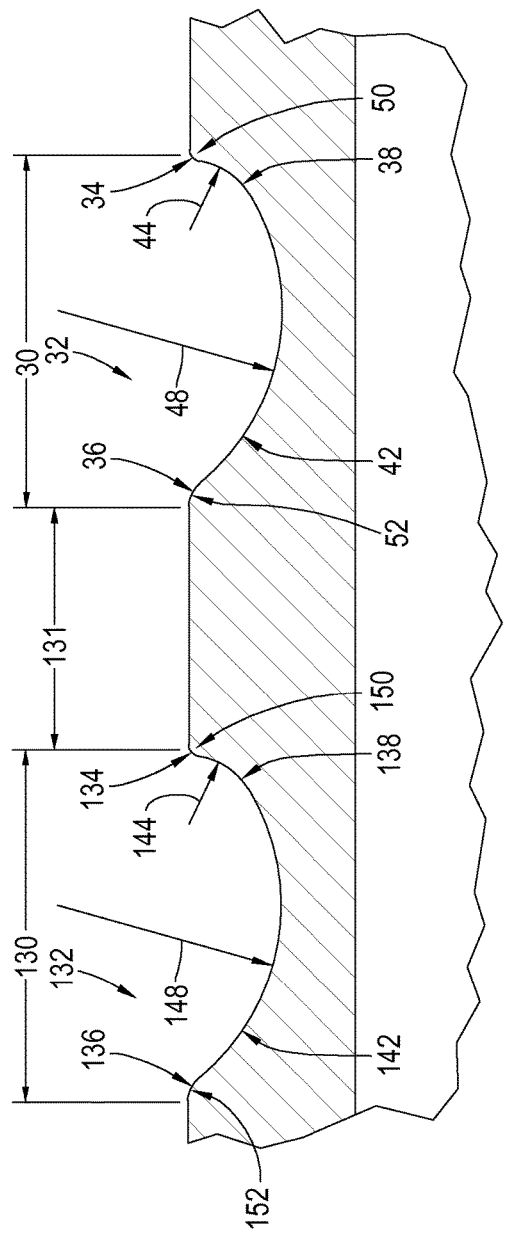

SHAPED ECHOGENIC NEEDLE GROOVE

CROSS-REFERENCE TO RELATED APPLICATION

This application claims the benefit of U.S. Provisional Patent Application No. 62/049,573 filed Sep. 12, 2014, which is hereby incorporated by reference.

FIELD

The present disclosure concerns devices and methods for ultrasound use within the human body, including devices and methods for enhancing ultrasound visibility.

BACKGROUND

Medical devices for subcutaneous use are known in the medical field. For example, biopsy needles are used to capture and remove internal tissues while avoiding invasive surgery. When performing medical procedures, often targeted bodily areas are surrounded by blood vessels or internal organs which can cause difficulties with accurate percutaneous positioning of medical devices. Imaging methods can mitigate some of these difficulties by providing for simultaneous imaging of internal organs and medical devices. Ultrasound imaging is particularly suitable due to its lesser operation cost and increased portability in comparison to other imaging modalities such as X-ray and MRI. During ultrasound imaging procedures, a transducer emits ultrasound waves. A portion of the ultrasound waves reflect when encountering organs, tissues, and other items inside the body and then return to the transducer. The returned sound waves are then used to produce a visual representation of an internal cavity. This provides a real-time moving image of the internal organs and medical device which a physician can use to guide the medical device to the desired bodily area.

Problems exist with current uses of ultrasound imaging to place a medical device subcutaneously because the image obtained through ultrasound is not always clear. Several factors can affect ultrasonic visibility of a medical device. For example, the density of the material that the device is constructed of, the surface structure of the device, and the angle of the device relative to the transducer each affect ultrasonic visibility of the device. When the image clarity suffers, the observation and positioning of the medical device can be more imprecise. This can enhance the risk of inadvertent damage to surrounding tissues or incorrect tissue excision in the case of biopsy.

To increase image clarity, echogenic enhancements which cause an altered or improved reflective response of ultrasound waves can be applied to a medical device and can cause greater ultrasound image clarity of the device. This in turn can increase accuracy when positioning the medical device. For example, it is known to apply echogenic enhancements near the tip of a needle so that the tip location is known with greater accuracy. However, if the needle angle changes relative to the transducer angle, the quality of the signal reflected back to the transducer degrades. As another example, it is known to apply echogenic enhancements that extend above a needle surface to increase echogenicity; however, during use in a patient these enhancements can apply drag force and thereby cause tenting of a blood vessel into body tissue upon needle removal. Drag force or tenting of the blood vessel or other body tissue is painful for the medical patient and causes trauma to vessels and body tissue. Additionally, while ultrasound technology has advanced to allow use of a wider range of ultrasound frequencies, standard echogenic enhancements allow the device to be clearly shown under a limited range of transducer frequencies. Thus, there is a need for echogenically-enhanced medical devices which can provide an ultrasound image that is more consistent and having better quality across a range of insertion angles and frequencies and body areas. Such echogenically-enhanced medical devices can improve the physician's confidence in placing a medical device.

Thus, there is a need for improvement in this field.

SUMMARY

Among other things, disclosed are devices and methods for enhancing echogenicity of medical devices. In one example, a medical device has a device surface with at least two adjacent echogenic features with an intervening section positioned between the echogenic features. Each of the echogenic features is formed as a depression positioned between a first transition lip and a second transition lip wherein the first and the second transition lips each have a convex shape. Each of the at least two echogenic features has a length that is within about 0.1 mm of a length of the intervening section. In one embodiment, the depression has a steep portion adjacent a shallow portion wherein the steep portion has a first radius and the shallow portion has a second radius that is larger than the first radius. An example range of values for the first radius is between 0.04 mm to 0.15 mm and the second radius is between 0.3 mm to 0.4 mm; however, the first and second radii can be sized differently in other embodiments. In one embodiment, the first radius is about 0.08 mm. The intervening section has a planar surface wherein each of the first and the second transition lips extend to the intervening section but do not extend above the surface of the intervening section. Some example shapes of the depression can include triangular, parallelogram, parabolic, or round, to name a few.

In another example, a medical device includes a device surface having a first echogenic feature adjacent a second echogenic feature and an intervening section that spans between the first and the second echogenic features. The first echogenic feature is formed as a first depression positioned between a first transition lip and a second transition lip wherein the first transition lip has a first radius and the second transition lip has a second radius that is sized differently from the first radius. The second echogenic feature is formed as a second depression positioned between a third transition lip and a fourth transition lip wherein the third transition lip has a third radius and the fourth transition lip has a fourth radius that is sized differently from the third radius. The intervening section has a planar surface that extends to the second transition lip and the third transition lip. In one form, the first echogenic feature has a length substantially equal to a length of the intervening section.

In some embodiments, the medical device is a needle having a longitudinal axis along a length thereof and the device surface extends around an entire circumference of the needle, wherein the first echogenic feature, the intervening section, and the second echogenic feature also extend around the entire circumference of the needle. Additionally, the first echogenic feature can form a first helical grove and the second echogenic feature forms a second helical groove. In any embodiment, the first echogenic feature can have a different cross-sectional shape than the second echogenic feature. In one embodiment, the first depression has a steep portion adjacent a shallow portion wherein the steep portion has a first radius and the shallow portion has a second radius that is larger than the first radius. Additionally, the second depression has a steep portion adjacent a shallow portion, the steep portion has a third radius, and the shallow portion has a fourth radius that is larger than the third radius, wherein the third radius is sized differently from the first radius and the fourth radius is sized differently from the second radius.

In other embodiments, the medical device includes a device surface having a plurality of echogenic features and a plurality of intervening sections, wherein each of the echogenic features is formed as a depression positioned between and continuous with a first transition lip and a second transition lip, wherein the first transition lip has a first radius and the second transition lip has a second radius that is smaller than the first radius. The plurality of echogenic features are distributed along at least a portion of a length of the device and separated from one another by one of the intervening sections, wherein one of the intervening sections has a planar surface with a length that is within 0.1 mm of a length of one of the echogenic features. In one form, each of the first and the second transition lips form a smooth interface with one of the intervening sections. In any form, the medical device is a needle having a longitudinal axis along a length thereof, the device surface extends around an entire circumference of the needle, wherein the plurality of echogenic features and the plurality of intervening sections extend around the entire circumference of the needle. In this form, the plurality of echogenic features can form a helical groove. In any form, the depression has a concave surface that includes a steep portion and a shallow portion, wherein each of the steep and shallow portions has a unique radius.

Further forms, objects, features, aspects, benefits, advantages, and embodiments of the present disclosure will become apparent from a detailed description and drawings provided herewith.

BRIEF DESCRIPTION OF THE DRAWINGS

FIG. 1 is a side view of a medical device having echogenic regions.

FIG. 2 is partial cross-sectional view of the medical device of FIG. 1.

DESCRIPTION OF THE SELECTED EMBODIMENTS

Figure 3:
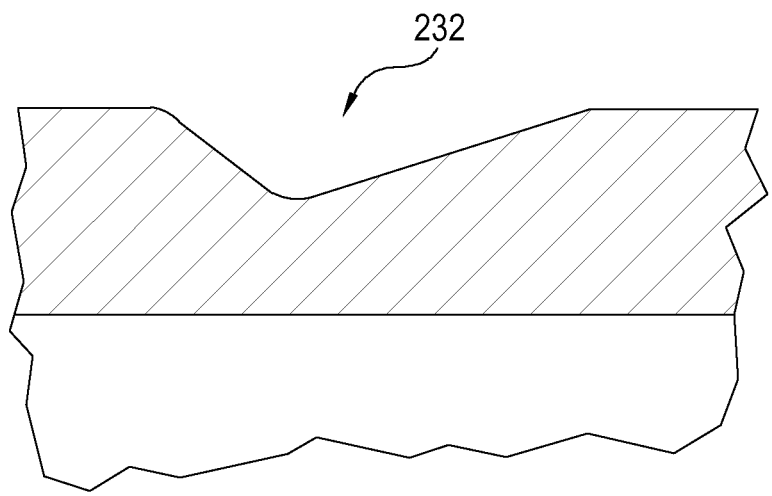
FIG. 3 is a partial cross-sectional view of a second embodiment of a medical device having echogenic features.

For the purpose of promoting an understanding of the principles of the disclosure, reference will now be made to the embodiments illustrated in the drawings and specific language will be used to describe the same. It will nevertheless be understood that no limitation of the scope of the claims is thereby intended. Any alterations and further modifications in the described embodiments, and any further applications of the principles of the disclosure as described herein are contemplated as would normally occur to one skilled in the art to which the disclosure relates. Embodiments are shown in detail, although it will be apparent to those skilled in the relevant art that some features that are not relevant to the present disclosure may not be shown for the sake of clarity.

Disclosed herein are embodiments of a medical device 20 suitable for endoluminal medical procedures. Device 20 has echogenic enhancements which make device 20 particularly suitable for use in conjunction with an ultrasound system. The echogenic enhancements include surface features which enhance, scatter, and/or redirect ultrasound signals. In some embodiments, the sizes of the features are varied to provide enhanced ultrasound signals at various ultrasound frequencies. The features are shaped and arranged to provide enhanced ultrasound signals at various spatial configurations (i.e. angles) between device 20 and an ultrasound transducer. In some cases, device 20 is used with a system that includes an ultrasound console (not shown) to provide subcutaneous imaging of device 20. The console portion can be connected to commercially available ultrasound probes with compatible printout, or other medical devices which are configured for ultrasound imaging. The console is configured to process data obtained from an ultrasound transducer and in some cases creates image(s) viewable on a display or other data output.

As used herein, the term "echogenic" describes the characteristic ability of a surface or device to direct a relatively favorable quality and quantity of an ultrasound signal back to a transducer for imaging purposes in comparison to a surface or device (or portion thereof) which is less echogenic, non-echogenic, or echolucent. In other words, a device or surface with increased echogenicity (or greater echogenic response) provides enhanced ultrasound imaging capabilities compared to a device or surface which is less echogenic or more echolucent. As used herein, "echogenic" and "echogenicity" typically refers to characteristics of device 20 when device 20 is positioned within a body conduit or other such environment where fluids and/or body tissues surround device 20.

Referring generally to FIGS. 1 and 2, embodiments of medical device 20 are illustrated. FIG. 1 shows an exemplary embodiment of device 20 which is in the form of a needle. It should be understood that device 20 could be any of a variety of types of medical devices which are used for percutaneous, subcutaneous or other internal applications involving ultrasound imaging and therapeutic techniques (e.g. biopsy needles, intravascular devices, laparoscopic tools, etc.). Device 20 in this embodiment includes a body 21, a tip 26, and a handle 23. Particular embodiments of device 20 are cylindrical and are sized for insertion into a body without the need for an existing body conduit such as a blood vessel.

Body 21 in the illustrated embodiments is an elongated member, e.g. a tube or cannula having an outer surface 24 (i.e. device surface) and an inner surface 22 defining a lumen 25 (FIG. 1). Body 21 terminates at a tip 26. Body 21 can be constructed of any suitable metal or polymer which is biocompatible and otherwise structurally appropriate for use as described herein.

Device 20 includes a control end which during use is nearest to the user and an application end which during use is nearest to the user's point of interest. The terms "control" and "application" are used throughout this description to describe these positional orientations. The control end of device 20 may extend outside of the patient during use. Alternatively, the control end may attach to another piece that extends outside the patient. The control end generally ends in a handle 23 or other operating portion for maneuvering device 20. Handle 23 can be any of a variety of forms or structures suitable for use in conjunction with needles or medical devices used in percutaneous applications. Handle 23 is generally constructed to be manipulatable by hand in some embodiments and has a hollow axis in communication with lumen 25 which can receive a stylet or other cylindrical objects.

The application end of the body 21 is formed as a beveled tip 26 in some embodiments. The bevel is generally constructed by cutting the cannula along a plane oblique to the lumen axis, i.e. a plane having a normal axis that is non-parallel to the lumen axis. Other embodiments of a body 21 may have alternative configurations. Tip 26 has cutting edges where the angle between the bevel surface and the outer surface is acute. Typically such bevels are capable of piercing or slicing tissue. Although the embodiment of tip 26 described herein is generally a planar cut configuration, other configurations of needle tips with varied cutting edges could be used.

Device 20 has one or more echogenic regions (e.g. echogenic regions 29) which are populated with one or more echogenic features 30 that enhance the echogenicity of device 20. The echogenic region is at least a portion of device 20, and in particular embodiments is at least a portion of surface 24. Device 20 also includes one or more intervening sections 31 that are formed on a portion of surface 24. As illustrated, the echogenic features 30 and the intervening sections 31 are arranged in an alternating arrangement, as described in more detail below.

Echogenic feature 30 includes a depression 32 in surface 24, which can have any of several possible geometric configurations. Echogenic feature 30 also includes a first transition lip 34 and a second transition lip 36 wherein the depression 32 spans between lips 34 and 36. In the embodiment shown in FIGS. 1 and 2, depression 32 has a concavely curved surface or feature surface formed by a steep portion 38 positioned adjacent to a shallow portion 42 wherein the steep portion 38 has a radius 44 and the shallow portion 42 has a radius 48. As illustrated, the radius 44 is smaller than the radius 48. In this unique configuration, the smaller radius 44 captures the higher frequency of ultrasound and the larger radius 48 captures the lowest or lower frequency of the ultrasound. In one embodiment, the radius 44 is between about 0.04 millimeters (mm) to about 0.15 mm which will reflect sound waves from a transducer in the range of about 4 to 20 MHz. In one particular embodiment the radius 44 is about 0.08 mm. In another or the same embodiment, the radius 48 is between about 0.3 mm to 0.4 mm which will reflect sound waves from a transducer in the range of about 2 to 3 MHz.

In one embodiment, the overall length of the echogenic feature 30 as measured along the longitudinal axis L of the device 20 is between about 0.075 millimeters and 0.3 mm. The largest depth of the depression 32 corresponds to the intersection of the steep portion 38 and the shallow portion 42. The maximum depth of the depression 32 will extend from the needle outer surface 24 to close to the inner surface 22 but will not extend into the lumen 25. In one embodiment, the depth of the depression 32 is between 5% and 30% of the wall thickness of the device 20.

Alternative shapes for depression 32 include parabolic, triangular, parallelogram, round, or curved. In one embodiment, the depression 32 has a parabolic shape with a central axis that is rotated relative to a longitudinal axis, L, of the device 20. In this configuration, a smaller radius of the parabolic shape captures the higher frequency of ultrasound and a larger radius of the parabolic shape captures the lower frequency of the ultrasound. In another embodiment illustrated in FIG. 3, a depression 232 has a triangular cross-sectional shape. In yet another embodiment, the depression 32 is a curved surface formed by three or more radii wherein the radii are sized differently.

Also illustrated in FIG. 2 is a second echogenic feature 130 that is similar to echogenic feature 30; however, in alternative embodiments second echogenic feature 130 can have a different geometric configuration than echogenic feature 30. Second echogenic feature 130 includes a depression 132 in surface 24. Second echogenic feature 130 also includes a third transition lip 134 and a fourth transition lip 136 wherein the depression 132 spans between lips 134 and 136. In the embodiment shown in FIG. 2, depression 132 has a concavely curved surface or feature surface formed by a steep portion 138 adjacent to a shallow portion 142 wherein the steep portion 138 has a radius 144 and the shallow portion 142 has a radius 148. As illustrated, the radius 144 is smaller than the radius 148. In this unique configuration, the smaller radius 144 captures the higher frequency of ultrasound and the largest radius 148 captures the lowest or lower frequency of the ultrasound. In other embodiments, any portion of depression 132 can vary in size or shape from depression 32.

In one embodiment, the radius 144 is between about 0.04 millimeters (mm) to about 0.15 mm which will reflect sound waves from a transducer in the range of about 4 to 20 MHz. In one particular embodiment the radius 144 is about 0.08 mm. In another or the same embodiment, the radius 148 is between about 0.3 mm to 0.4 mm which will reflect sound waves from a transducer in the range of about 2 to 3 MHz.

In one embodiment, the overall length of the echogenic feature 130 as measured along the longitudinal axis L of the device 20 is between about 0.075 millimeters and 0.3 mm. The largest depth of the depression 132 corresponds to the intersection of the steep portion 138 and the shallow portion 142. The maximum depth of the depression 132 will extend from the needle outer surface 24 to close to the inner surface 22 but will not extend into the lumen 25. In one embodiment, the depth of the depression 132 is between 5% and 30% of the wall thickness of the device 20.

The first transition lip 34 has a first radius 50 and the second transition lip 36 has a second radius 52. In the illustrated embodiment, the second radius 52 is larger than the first radius 50; however, both first transition lip 34 and second transition lip 36 are convex curves relative to the longitudinal axis L of the device 20. The outwardly curved nature of the first transition lip 34 and the second transition lip 36 increases the echogenicity of the device 20 by capturing varying frequencies of ultrasound. Moreover, first transition lip 34 forms a smooth transition with the intervening section 31 wherein the first transition lip 34 does not extend above the needle surface 24. First transition lip 34 also connects with and forms a smooth transition to steep portion 38. Similarly to first transition lip 34, second transition lip 36 forms a smooth transition with the intervening section 31 wherein the second transition lip 36 does not extend above the needle surface 24. Second transition lip 36 also connects with shallow portion 42 and forms a smooth transition therewith.

Beneficially, the smooth transitions from the first and second transition lips 34 and 36 relative to the corresponding and adjacent intervening section 31 reduce or eliminate drag force during use of the device 20 as the medical device 20 is either inserted into a patient or removed from the patient. Some prior art devices include ridges or bumps that extend above the needle or device surface which will increase echogenicity but also increase drag force which is painful for the patient and can cause tenting or damage of the vessels or other internal body parts upon insertion or removal of the device from a patient.

Similarly to first transition lip 34 and second transition lip 36, the third transition lip 134 and the fourth transition lip 136 have a third radius 150 and a fourth radius 152, respectively. In the illustrated embodiment, the fourth radius 152 is larger than the third radius 150; however, both third transition lip 134 and fourth transition lip 136 are convex curves relative to the longitudinal axis L of the device 20. The outwardly curved nature of the third transition lip 134 and the fourth transition lip 136 increases the echogenicity of the device 20 by capturing varying frequencies of ultrasound. Moreover, third transition lip 134 forms a smooth transition with an intervening section 131 wherein the third transition lip 134 does not extend above the needle surface 24. Third transition lip 134 also connects with and forms a smooth transition to steep portion 138. Similarly to third transition lip 134, fourth transition lip 136 forms a smooth transition with an adjacent intervening section or needle surface 24 wherein the fourth transition lip 136 does not extend above the needle surface 24. Fourth transition lip 136 also connects with shallow portion 142 and forms a smooth transition therewith.

As discussed previously, the intervening section 31 has a planar surface on the needle surface 24, and the unique configuration of the first transition lip 34 and second transition lip 36 that do not extend above the surface of the intervening section 31 provide benefits to the user. For example, during use of the device 20, the combination of the planar surface of intervening section 31 and the configuration of the lips 34 and 36 reduce tenting of a bodily vessel or body tissue when the device or needle 20 is inserted into and/or removed from a patient.

In one embodiment, the length of one echogenic feature 30 is substantially the same or within about 0.1 mm of the length of one intervening section 31. In a further embodiment, a plurality of intervening sections 31 and a plurality of echogenic features 30 are arranged in an alternating relationship wherein the length of each of the echogenic features 30 is within about 0.1 mm of the length of each of the intervening sections 31. In other embodiments, the length of each of the echogenic features 30 is within about 0.1 to 0.3 mm of the length of the intervening sections 31. Beneficially it has been found that these configurations increase echogenicity of the device 20 and improve image quality with ultrasound. Arranging of the plurality of intervening sections 31 and the plurality of echogenic features 30 in an alternating relationship with a known spacing between features 30 provides echogenic markers for use by a medical professional on a patient.

In various embodiments, features 30 can be organized and positioned in a variety of configurations. The echogenic features 30 can be positioned at any point between the application side end of device 20 and the control side end of device 20. The echogenic features 30 can occupy a portion or all of tip 26, a region adjacent to tip 26, or other parts of device 20. In the embodiment of FIGS. 1 and 2, an echogenic region 29 is positioned near tip 26 so that not only can device 20 be located during ultrasound procedures but also tip 26 can be more accurately positioned during ultrasound procedures. In some embodiments, one or more echogenic regions 29 are also positioned further from tip 26, and can be spaced a known distance apart to provide information to a user during ultrasound procedures, such as the distance of insertion of a needle or the proximity of the tip to certain body tissues (e.g. FIG. 1).

The embodiment of FIG. 1 shows features 30 arranged as a plurality of helical grooves 60 within the echogenic regions 29, with each feature 30 representing a helical groove 60 in the surface 24. The embodiment of FIG. 1 also shows intervening section 31 arranged as a plurality of intervening sections 31 that extend around the perimeter of the device 20 to form a plurality of helical smooth surfaces 62. In any embodiment, a pitch angle, P, of the helical groove 60 can vary along the length of the device or needle 20. In other embodiments, the plurality of helical grooves 60 can include multiple grooves wherein each of the grooves is sized or shaped differently or uniquely. The helical groove 60 can have a constant pitch or helical angle, multiple pitch angles (increasing or decreasing pitch angle) and/or include multiple grooves. In some embodiments, features 30 can be arranged to span longitudinally along surface 24 and along the longitudinal axis. In other embodiments, the depth of features 30 varies over the echogenic range 29. This variance can extend even to features 30 having the same transition lip size. Similarly, the relative angles between the walls (or surfaces) of features 30 can vary.

During use, device 20 is inserted into a body conduit either through puncture or through an existing body conduit. An ultrasound imaging system including a console is used to image device 20 during insertion and while maneuvering device 20 to a desired location within the body. The ultrasound imaging system includes a transducer which is applied to the external surface of the body. The transducer transmits ultrasound signals generally towards device 20. Device 20 scatters and/or reflects a certain amount of the ultrasound signal back to the transducer. The transducer receives the returned ultrasound signal and transmits appropriate information to the console. The console displays an image which shows device 20 surrounded by body tissues and fluids. It is preferable for device 20 to appear with greater clarity and brightness than the surrounding body tissues and fluids. This is achieved by providing device 20 with enhanced echogenic properties. Features 30, including depressions 32, first transition lip 34, and second transition lip 36, and similarly features 130 including depressions 132, third transition lip 134, and fourth transition lip 136 provide device 20 with enhanced echogenic properties. Use of such echogenic features enhances echogenicity as compared to a smooth surface for a similar object.

Device 20 having echogenic features 30 and 130 is capable of providing enhanced ultrasound visualization throughout a wide range of ultrasound frequencies and relative angles between device 20 and the transducer. In some embodiments of device 20 wherein the features 30 and 130 are of approximately the same length or within about 10% or 0.1 mm to about 0.3 mm of the length of the intervening sections 31 and 131, respectively, an improved image quality of the returned ultrasound signal is displayed on the console. As mentioned previously, the first transition lip 34 and the second transition lip 36 have a convexly curved shape relative to the longitudinal axis, L, of the device 20, which during use of the device 20 reduces drag force on the surrounding body tissue or vessels when the device 20 is inserted into or removed from a body conduit.

Turning now to a method of manufacture of the unique device, in one embodiment, the echogenic feature 30 is manufactured by a roll machine. Echogenic feature 30 is rolled into the device 20 using a machine that applies radial force at a helical or helix angle while rotating a roller or cylinder that engages the outer surface 24 of the device 20. The roller includes at least one nub that extends outwardly from the surface of the roller and also extends around the circumference of the roller to engage the device 20. The nub is configured such that the periphery of the nub is a shape that is the reverse image of the depression 32 that is to be pressed into the outer surface 24 of the device 20. The nub has a shape that presses or knurls into the outer surface 24 and into the wall thickness of the device 20 to form depression 32 or groove 60. The intersection of the nub and the roller that correspondingly engages the outer surface 24 forms the transition lips 34 and 36 adjacent the depression 32 for device 20.

Device 20 is placed in a gripper of the roll machine and the roller presses the nub into the device 20 to form the depression 32 or groove 60 while rotating the device 20. As the roller spins it drives the device 20 to spin and be drawn into the roller axially at the set helical or helix angle. As the device 20 is drawn into the roller axially and the nub presses into the outer surface 24, the overall length of the device 20 increases by the displacement of material from the transition lips 34 and 36. The wall thickness of the device 20 stays about the same during the manufacturing process. In one embodiment, the lumen 25 in a finished device 20 has a smooth inner surface 22 to receive a stylet. As such, the clearance between the stylet and the inner surface 22 is within industry standards. The helical angle can be increased, decreased or reversed to reverse the axial direction of the grooves 60 and generate additional helical grooves. Multiple nubs on the roller can be employed to generate multiple cross-sectional groove shapes during the same operation; for example parabolic, triangular, multiple radii, and rounded cross-sectional shaped grooves. Beneficially multiple groove shapes in a single device 20 reflects a wider range of ultrasound frequencies at a greater range of insertion angles therefore increasing the echogenicity of the device 20 when in use. Upon reaching the dimensional end of the echogenic regions 29 the roller is radially withdrawn to release the device 20.

It is known to remove material from needles or cannulas to create features in the needle surface by various techniques. Some techniques include laser ablation, grinding, and/or machining grooves into a surface of a medical device, such as a cannula or needle, wherein removal of material can cause by-products or waste material which can become trapped in the grooves or lumen of the medical device. The present technique of manufacturing the device 20 by a roll machine avoids these undesirable effects.

Although particular materials were highlighted herein for some components of device 20, those materials are not intended to be limiting of the types of materials which are suitable to be used in device 20. Additionally, where materials were not highlighted, a variety of materials could be used such as certain types of metals, in particular, nitinol, polymers, ceramics or other types of materials which are suitable for use in devices for small body cavity applications.

While the disclosure has been illustrated and described in detail in the drawings and foregoing description, the same is to be considered as illustrative and not restrictive in character, it being understood that all changes, equivalents, and modifications that come within the spirit of the inventions defined by following claims are desired to be protected. All publications, patents, and patent applications cited in this specification are herein incorporated by reference as if each individual publication, patent, or patent application were specifically and individually indicated to be incorporated by reference and set forth in its entirety herein.

The invention claimed is:

1. A medical device, comprising:
a device surface having at least two adjacent echogenic features with an intervening section positioned between the echogenic features, each of the echogenic features formed as a depression positioned between a first transition lip and a second transition lip, the first transition lip and the second transition lips each having a convex shape, wherein each of the at least two adjacent echogenic features has a length that is within 0.1 mm of a length of the intervening section, and wherein the depression has a steep portion adjacent a shallow portion, the steep portion has a first radius and the shallow portion has a second radius that is larger than the first radius.

2. The medical device of claim 1, wherein the first radius is between 0.04 mm to 0.15 mm and the second radius is between 0.3 mm to 0.4 mm.

3. The medical device of claim 1, wherein the first radius is about 0.08 mm.

4. The medical device of claim 1, wherein the intervening section has a planar surface and each of the first transition lip and the second transition lip extend to the intervening section.

5. The medical device of claim 1, wherein the depression has a triangular shape.

6. The medical device of claim 1, wherein the depression has a parallelogram shape.

7. The medical device of claim 1, wherein the length of each of the at least two adjacent echogenic features is between 0.075 millimeters and 0.30 millimeters.

8. The medical device of claim 1, which is a needle, and wherein said device surface is a metal surface.

9. A medical device, comprising:
a device surface having a first echogenic feature adjacent a second echogenic feature and an intervening section that spans between the first echogenic feature and the second echogenic feature, the first echogenic feature formed as a first depression positioned between a first transition lip and a second transition lip, the first transition lip has a first radius and the second transition lip has a second radius that is sized differently from the first radius, the second echogenic feature formed as a second depression positioned between a third transition lip and a fourth transition lip, the third transition lip has a third radius and the fourth transition lip has a fourth radius that is sized differently from the third radius, wherein the intervening section has a planar surface that extends to the second transition lip and the third transition lip.

10. The medical device of claim 9, wherein the first echogenic feature has a length within about 0.1 to 0.3 mm of a length of the intervening section.

11. The medical device of claim 9, wherein the medical device is a needle having a longitudinal axis along a length thereof, the device surface extends around an entire circumference of the needle, wherein the first echogenic feature, the intervening section, and the second echogenic feature extend around the entire circumference of the needle.

12. The medical device of claim 9, wherein the first echogenic feature forms a first helical grove and the second echogenic feature forms a second helical groove.

13. The medical device of claim 9, wherein the first echogenic feature has a different cross-sectional shape than the second echogenic feature.

14. The medical device of claim 9, wherein the first depression has a steep portion adjacent a shallow portion, the steep portion has a first radius and the shallow portion has a second radius that is larger than the first radius.

15. The medical device of claim 9, wherein the second depression has a steep portion adjacent a shallow portion, the steep portion has a third radius and the shallow portion has a fourth radius that is larger than the third radius, wherein the third radius is sized differently from the first radius and the fourth radius is sized differently from the second radius.

16. A medical device, comprising:
a device surface having a plurality of echogenic features and a plurality of intervening sections, wherein each of the echogenic features is formed as a depression positioned between and continuous with a first transition lip and a second transition lip, wherein the first transition lip has a first radius and the second transition lip has a second radius that is smaller than the first radius, the plurality of echogenic features distributed along at least a portion of a length of the medical device and separated from one another by one of the intervening sections, wherein one of the intervening sections has a planar surface with a length that is within 0.1 mm of a length of one of the echogenic features.

17. The medical device of claim 16, wherein each of the first transition lip and the second transition lip form a smooth interface with one of the intervening sections.

18. The medical device of claim 16, wherein the medical device is a needle having a longitudinal axis along a length thereof, the device surface extends around an entire circumference of the needle, wherein the plurality of echogenic features and the plurality of intervening sections extend around the entire circumference of the needle.

19. The medical device of claim 16, wherein the plurality of echogenic features forms a helical groove.

20. The medical device of claim 16, wherein the depression has a concave surface that includes a steep portion and a shallow portion, wherein the steep portion has a first radius, wherein the shallow portion has a second radius, and wherein the first radius is different from the second radius.

* * * * *